US012564443B2

(12) United States Patent
Falkenstein et al.

(10) Patent No.: US 12,564,443 B2
(45) **Date of Patent: \*Mar. 3, 2026**

(54) TAILORED LASER PULSES FOR SURGICAL APPLICATIONS

(71) Applicant: Boston Scientific Scimed, Inc., Maple Grove, MN (US)

(72) Inventors: Werner Falkenstein, Feldafing (DE); Michael Schubert, Tutzing (DE); Stephan Dittmar, Gauting (DE); Anna Butsch, Regensburg (DE); Thomas Kremser, Koenigsdorf (DE)

(73) Assignee: Boston Scientific Scimed, Inc., Maple Grove, MN (US)

( \* ) Notice: Subject to any disclaimer, the term of this patent is extended or adjusted under 35 U.S.C. 154(b) by 119 days.

This patent is subject to a terminal disclaimer.

(21) Appl. No.: 18/404,408

(22) Filed: Jan. 4, 2024

(65) Prior Publication Data

US 2024/0130785 A1     Apr. 25, 2024

Related U.S. Application Data

(63) Continuation of application No. 17/121,815, filed on Dec. 15, 2020, now Pat. No. 11,896,300, which is a
(Continued)

(51) Int. Cl.
*A61B 18/20* (2006.01)
*A61B 18/26* (2006.01)
(Continued)

(52) U.S. Cl.
CPC .............. *A61B 18/20* (2013.01); *A61B 18/26* (2013.01); *H01S 3/10038* (2013.01);
(Continued)

(58) Field of Classification Search
CPC ....... A61B 18/20; A61B 18/26; A61B 18/245; A61B 2017/00176; A61B 2018/00642;
(Continued)

(56) References Cited

U.S. PATENT DOCUMENTS 4,058,774 A * 11/1977 Hughes ................. H01S 3/2333
                                                              356/28
4,197,513 A * 4/1980 Bell ........................ H01S 3/115
                                                              372/12
(Continued)

FOREIGN PATENT DOCUMENTS

CN         1729946 A      2/2006
CN       101015474 A      8/2007
(Continued)

OTHER PUBLICATIONS

Office Action in Japanese Application No. 2019-517928, mailed on Oct. 6, 2021 (2 pages).
(Continued)

*Primary Examiner* — Michael J Lau
(74) *Attorney, Agent, or Firm* — Seager, Tufte & Wickhem, LLP

(57)                    ABSTRACT

A laser system may include a controller configured to direct a plurality of temporally spaced-apart electrical pulses to a device that optically pumps a lasing medium, and a lasing medium configured to output a quasi-continuous laser pulse in response to the optical pumping. The plurality of temporally spaced-apart electrical pulses may include (a) a first electrical pulse configured to excite the lasing medium to an energy level below a lasing threshold of the lasing medium, and (b) multiple second electrical pulses following the first electrical pulse. The quasi-continuous laser pulse is output in response to the multiple second electrical pulses.

20 Claims, 6 Drawing Sheets

Related U.S. Application Data continuation of application No. 15/723,700, filed on Oct. 3, 2017, now Pat. No. 10,893,906.

(60) Provisional application No. 62/403,916, filed on Oct. 4, 2016.

(51) Int. Cl.

| | |
|---|---|
| *H01S 3/10* | (2006.01) |
| *H01S 3/102* | (2006.01) |
| *A61B 17/00* | (2006.01) |
| *A61B 18/00* | (2006.01) |
| *A61B 18/22* | (2006.01) |
| *A61B 18/24* | (2006.01) |
| *H01S 3/04* | (2006.01) |
| *H01S 3/042* | (2006.01) |
| *H01S 3/093* | (2006.01) |
| *H01S 3/131* | (2006.01) |
| *H01S 3/16* | (2006.01) |

(52) U.S. Cl.

CPC .. *H01S 3/1024* (2013.01); *A61B 2017/00176* (2013.01); *A61B 2018/00642* (2013.01); *A61B 2018/0066* (2013.01); *A61B 2018/00702* (2013.01); *A61B 2018/00714* (2013.01); *A61B 2018/00791* (2013.01); *A61B 2018/205545* (2017.05); *A61B 2018/2261* (2013.01); *A61B 2018/2277* (2013.01); *A61B 18/245* (2013.01); *H01S 3/0407* (2013.01); *H01S 3/042* (2013.01); *H01S 3/093* (2013.01); *H01S 3/1312* (2013.01); *H01S 3/1616* (2013.01); *H01S 3/1643* (2013.01)

(58) Field of Classification Search

CPC .. A61B 2018/0066; A61B 2018/00702; A61B 2018/00714; A61B 2018/00791; A61B 2018/205545; A61B 2018/2261; A61B 2018/2277; H01S 3/10038; H01S 3/1024; H01S 3/0407; H01S 3/042; H01S 3/093; H01S 3/1312; H01S 3/1616; H01S 3/1643

See application file for complete search history.

(56) References Cited

U.S. PATENT DOCUMENTS

| | | | |
|---|---|---|---|
| 4,313,093 A | | 1/1982 | Suenaga et al. |
| 4,785,456 A | | 11/1988 | Kaplan |
| 5,151,909 A | | 9/1992 | Davenport et al. |
| 5,390,204 A | | 2/1995 | Yessik et al. |
| 5,400,351 A | | 3/1995 | Montgomery et al. |
| 5,720,894 A | | 2/1998 | Neev et al. |
| 5,982,790 A | | 11/1999 | Grossman et al. |
| 6,055,815 A | | 5/2000 | Peterson |
| 6,122,300 A | * | 9/2000 | Freiberg ................ H01S 3/1022 |
| | | | 372/92 |
| 6,193,711 B1 | | 2/2001 | Connors et al. |
| 6,792,027 B2 | * | 9/2004 | Lai ............................ H01S 3/23 |
| | | | 372/99 |
| 6,998,567 B2 | | 2/2006 | Yeik |
| 8,613,741 B1 | | 12/2013 | Jones et al. |
| 9,048,622 B2 | | 6/2015 | Nakai |
| 9,246,303 B1 | * | 1/2016 | Rockwell ................ G01S 7/484 |
| 9,310,167 B1 | * | 4/2016 | Farmer ................. H01S 5/0427 |
| 9,397,469 B1 | | 7/2016 | Nijjar et al. |
| 10,305,244 B2 | * | 5/2019 | Sierra ................... H01S 3/0627 |
| 10,893,906 B2 | * | 1/2021 | Falkenstein ......... H01S 3/10038 |
| 11,129,675 B2 | * | 9/2021 | Varghese ............ A61B 18/203 |
| 11,896,300 B2 | * | 2/2024 | Falkenstein .......... H01S 3/1024 |
| 11,931,096 B2 | * | 3/2024 | Callas ................... A61B 18/14 |
| 2002/0049434 A1 | * | 4/2002 | Teichmann ............ A61B 18/20 |
| | | | 606/10 |
| 2002/0097471 A1 | | 7/2002 | Bethea et al. |
| 2003/0135205 A1 | | 7/2003 | Davenport et al. |
| 2003/0193975 A1 | | 10/2003 | Pang |
| 2003/0227953 A1 | | 12/2003 | Hsia et al. |
| 2004/0028101 A1 | | 2/2004 | Byren et al. |
| 2004/0151217 A1 | | 8/2004 | Yeik |
| 2005/0226280 A1 | | 10/2005 | Spariosu et al. |
| 2006/0084959 A1 | * | 4/2006 | Davenport ............. A61B 18/20 |
| | | | 606/15 |
| 2006/0176913 A1 | | 8/2006 | Souhaite et al. |
| 2006/0195072 A1 | | 8/2006 | Miller |
| 2007/0223544 A1 | | 9/2007 | Yamazaki et al. |
| 2008/0037597 A1 | | 2/2008 | Mason et al. |
| 2008/0095201 A1 | | 4/2008 | Mu et al. |
| 2009/0245300 A1 | | 10/2009 | Sun et al. |
| 2011/0098692 A1 | * | 4/2011 | Shazly ................... A61F 9/008 |
| | | | 606/10 |
| 2011/0134947 A1 | * | 6/2011 | Rahum ................. H01S 5/0612 |
| | | | 372/29.015 |
| 2012/0022511 A1 | | 1/2012 | Kang et al. |
| 2012/0165801 A1 | | 6/2012 | Bragagna et al. |
| 2012/0307851 A1 | | 12/2012 | Hori et al. |
| 2013/0128905 A1 | | 5/2013 | Moffatt |
| 2014/0185643 A1 | | 7/2014 | McComb et al. |
| 2014/0219299 A1 | | 8/2014 | Burkholder et al. |
| 2014/0243805 A1 | * | 8/2014 | Dick ...................... A61B 18/20 |
| | | | 606/11 |
| 2015/0100048 A1 | | 4/2015 | Hiereth et al. |
| 2015/0182283 A1 | * | 7/2015 | Boutoussov ........... A61B 18/22 |
| | | | 606/18 |
| 2015/0313672 A1 | * | 11/2015 | Milner ................... A61B 18/26 |
| | | | 606/2.5 |
| 2016/0073487 A1 | | 3/2016 | Yanagida et al. |
| 2016/0149367 A1 | | 5/2016 | Yin et al. |
| 2016/0149370 A1 | | 5/2016 | Marincek et al. |

FOREIGN PATENT DOCUMENTS

| | | | | | |
|---|---|---|---|---|---|
| DE | 10055179 A1 | * | 5/2002 | .......... | A61B 18/20 |
| JP | 52010983 A | | 1/1977 | | |
| JP | 2001168429 A | | 6/2001 | | |
| JP | 2008141127 A | | 6/2008 | | |
| JP | 2014524286 A | | 9/2014 | | |
| WO | WO-03100929 A1 | * | 12/2003 | .............. | H05G 2/00 |
| WO | WO-2009087072 A1 | * | 7/2009 | ........... | H01S 3/1127 |

OTHER PUBLICATIONS

Chinese Office Action in corresponding Chinese Application No. 201780061314.4 dated Oct. 9, 2021 (10 pages).

Sandu et al., "Holmium; YAG Laser for Intra Corporeal Lithotripsy," Medical Journal Armed Forces India, vol. 63, No. 1, 2007.

Koechner et al., "Solid-State Lasers: A Graduate Text," Springer, New York, pp. 78-103, 1937.

International Search Report and Written Opinion for corresponding International Application No. PCT/US2017/054889, dated Jan. 15, 2-18 (12 pages).

* cited by examiner

TAILORED LASER PULSES FOR SURGICAL APPLICATIONS

CROSS-REFERENCE TO RELATED APPLICATIONS

This patent application is continuation of U.S. application Ser. No. 17/121,815, filed Dec. 15, 2020, which is a continuation U.S. application Ser. No. 15/723,700, filed Oct. 3, 2017, which claims the benefit of priority under 35 U.S.C. § 119 to U.S. Provisional Patent Application No. 62/403, 916, filed Oct. 4, 2016, each of which is herein incorporated by reference in its entirety.

TECHNICAL FIELD

Various aspects of the present disclosure relate generally to laser systems and methods of using the laser systems for medical applications.

BACKGROUND

In medical applications, laser energy is used in many procedures. Non limiting examples of such procedures include incision, excision, resection, vaporization, ablation, fragmentation, coagulation, hemostasis, denaturization, etc. of various body tissues. In some medical procedures, lasers having, for example, a wavelength of about 2100 nanometer (nm) (or 2.1 micrometer ($\mu$m)) may be used, since energy of this wavelength is highly absorbed by water, a constituent of virtually all tissues.

In laser lithotripsy, laser energy is used to disintegrate stones in the urinary tract of a subject (patient, etc.). In some applications, laser lithotripsy may be performed using a Holmium YAG (Ho:YAG) laser which provides a relatively high fragmentation efficiency for different types of stones. See "Holmium:YAG Laser for Intra Corporeal Lithotripsy," Sandhu et al., Medical Journal Armed Forces India, Vol. 63, No. 1, 2007. The Ho:YAG laser is a solid-state, pulsed laser that emits light at 2100 nm. Although different commercial models vary slightly, commercially available Ho:YAG lasers have a pulse duration that ranges from 200-1700 microseconds ($\mu$s), pulse energy from 0.2-8.0 Joule/pulse, frequency from 3-100 Hz (single cavity resonators typically 3-30 Hz), and an average power between 15-140 Watts (single cavity resonators 15-50 W). Stone fragmentation effect typically depends on the energy of the applied laser. Conventionally, the laser energy is increased to increase efficiency (fragmentation efficiency, etc.). While high energies may lead to quick fragmentation, they may result in large stone fragments which may have to be extracted from the body using medical devices such as retrieval baskets. Lithotripsy, using high energy laser, may also cause undesirable retropulsion effects of the stone fragments. The systems and methods of the current disclosure may rectify some of these or other deficiencies in known laser systems. The scope of the current disclosure, however, is defined by the attached claims, and not by the ability to solve any specific problem.

SUMMARY

Examples of the present disclosure relate to, among other things, medical laser systems and their methods of use. Each of the examples disclosed herein may include one or more of the features described in connection with any of the other disclosed examples.

In one embodiment, a laser system is disclosed. The laser system may include a controller configured to direct a plurality of temporally spaced-apart electrical pulses to a device that optically pumps a lasing medium, and a lasing medium configured to output a quasi-continuous laser pulse in response to the optical pumping. The plurality of temporally spaced-apart electrical pulses may include (a) a first electrical pulse configured to excite the lasing medium to an energy level below a lasing threshold of the lasing medium, and (b) multiple second electrical pulses following the first electrical pulse. The quasi-continuous laser pulse is output in response to the multiple second electrical pulses.

Additionally or alternatively, embodiments of the system may include one or more of the following features: the lasing medium may include one of Ho:YAG, Tm:YAG, Tm:Ho: YAG, Er:YAG, Er:YLF, Nd:YAG, Tm-fiber laser, and CTH: YAG; each electrical pulse of the multiple second electrical pulses may have an electrical pulse duration between about 10-1000 $\mu$s; a spacing between adjacent electrical pulses of the multiple second electrical pulses may be between about 10-300 $\mu$s; a laser pulse duration of the quasi-continuous laser pulse may be between about 250 $\mu$s to 10 ms; a power of the quasi-continuous laser pulse may be between about 100 W to 1 KW; the quasi-continuous laser pulse may have a continuous waveform; the quasi-continuous laser pulse may include a plurality of temporally spaced apart laser pulses having a frequency greater than or equal to about 1 kHz; the first electrical pulse may be configured to excite the lasing medium to an energy level above about 80% of the lasing threshold and below the lasing threshold; and at least one of (i) duration, (ii) pulse-pulse spacing, and (iii) magnitude of a first set of pulses of the multiple second electric pulses may be different from a second set of pulses of the multiple second electric pulses.

In another embodiment, a method of using a laser system having a lasing medium is disclosed. The method may include directing a plurality of temporally spaced-apart electrical pulses to a device that optically pumps a lasing medium. The plurality of temporally spaced-apart electrical pulses may include (a) a first electrical pulse configured to excite the lasing medium to an energy level below a lasing threshold of the lasing medium, and (b) multiple second electrical pulses following the first electrical pulse. The method may also include outputting a quasi-continuous laser pulse from the lasing medium in response to the multiple second electrical pulses.

Additionally or alternatively, embodiments of the method may include one or more of the following features: each electrical pulse of the multiple second electrical pulses may have an electrical pulse duration between about 10-1000 $\mu$s, and a spacing between adjacent electrical pulses of the multiple second electrical pulses may be between about 10-300 $\mu$s; a laser pulse duration of the quasi-continuous laser pulse may be between about 250 $\mu$s to 10 ms, and a power of the quasi-continuous laser pulse may be between about 100 W to 1 KW; the quasi-continuous laser pulse may be one of (a) a single laser pulse having a continuous waveform, or (b) a plurality of temporally spaced apart laser pulses having a frequency greater than or equal to about 1 kHz; the first electrical pulse may be configured to excite the lasing medium to an energy level above about 80% of the lasing threshold and below the lasing threshold; the lasing medium may include one of Ho:YAG, Tm:YAG, Tm:Ho: YAG, Er:YAG, Er:YLF, Nd:YAG, Tm-fiber laser, and CTH: YAG; and at least one of (i) duration, (ii) pulse-pulse spacing, and (iii) magnitude of a first set of pulses of the multiple second electric pulses may be different from a second set of pulses of the multiple second electric pulses.

In another embodiment, a method of using a laser system having a lasing medium is disclosed. The method includes directing a plurality of temporally spaced-apart electrical pulses to a device that optically pumps a lasing medium. The plurality of temporally spaced-apart electrical pulses including (a) a first electrical pulse configured to excite the lasing medium to an energy level below a lasing threshold of the lasing medium, and (b) multiple second electrical pulses following the first electrical pulse. A first pulse of the multiple second electrical pulses may increase the energy level of the lasing medium above the lasing threshold. The method may also include outputting a quasi-continuous laser pulse from the lasing medium in response to the multiple second electrical pulses. The quasi-continuous laser pulse may be one of (a) a single laser pulse having a continuous waveform, or (b) a plurality of temporally spaced apart laser pulses having a frequency greater than or equal to about 1 kHz.

Additionally or alternatively, embodiments of the system may include one or more of the following features: each electrical pulse of the multiple second electrical pulses may have an electrical pulse duration between about 10-1000 μs, and a spacing between adjacent electrical pulses of the multiple second electrical pulses may be between about 10-300 μs; the quasi-continuous laser pulse may be a single laser pulse having a continuous waveform and may have a laser pulse duration between about 250 μs to 10 ms and a power between about 100 W to 1 KW; the first electrical pulse may be configured to excite the lasing medium to an energy level above about 80% of the lasing threshold and below the lasing threshold; the lasing medium may include one of Ho:YAG, Tm:YAG, Tm:Ho:YAG, Er:YAG, Er:YLF, Nd:YAG, Tm-fiber laser, and CTH:YAG; and at least one of (i) duration, (ii) pulse-pulse spacing, and (iii) magnitude of a first set of pulses of the multiple second electric pulses may be different from a second set of pulses of the multiple second electric pulses.

Both the foregoing general description and the following detailed description are exemplary and explanatory only and are not restrictive of the features, as claimed. As used herein, the terms "substantially," "approximately" and "about" refer to a variation of plus or minus ten percent over a stated value, and the term "exemplary" is used herein in the sense of "example," rather than "ideal."

BRIEF DESCRIPTION OF THE DRAWINGS

The accompanying figures, which are incorporated in and constitute a part of this specification, illustrate exemplary embodiments of the present disclosure. These figures, together with the description, serve to explain the principles of the disclosure. Some of these figures show components/elements that will be recognized by one skilled in the art. If detailed descriptions of such known components and elements are not necessary to an understanding of the present disclosure, they are not presented herein. Similarly, some components/elements which are known to persons skilled in the art as being part of the illustrated embodiments, but which are not necessary for describing the present disclosure are not illustrated in the figures for the sake of clarity.

DETAILED DESCRIPTION

Embodiments of the present disclosure, relate to a laser system used in any medical application. That is, a laser system of the present disclosure may have any type of lasing medium (e.g., Ho:YAG, Tm:YAG (Thulium doped YAG), CTH:YAG (Chromium, Thulium, Holmium doped YAG), Tm:Ho:YAG (Thulium and Holmium doped YAG), Er:YAG (Erbium doped YAG), Nd:YAG (Neodymium doped YAG), Er:YLF (Erbium doped Yttrium Lithium Fluoride), Tm-filer laser, etc.), optically pumped by any method (flashlamp, arclamp, diode, etc.), and may be used in any medical application. However, for convenience, only an optically pumped laser used in a lithotripsy procedure is described below to highlight the features of the present disclosure. Reference will now be made to exemplary embodiments of present disclosure illustrated in the accompanying drawings. Wherever possible, the same reference numbers will be used throughout the drawings to refer to the same or like parts.

Figure 1:
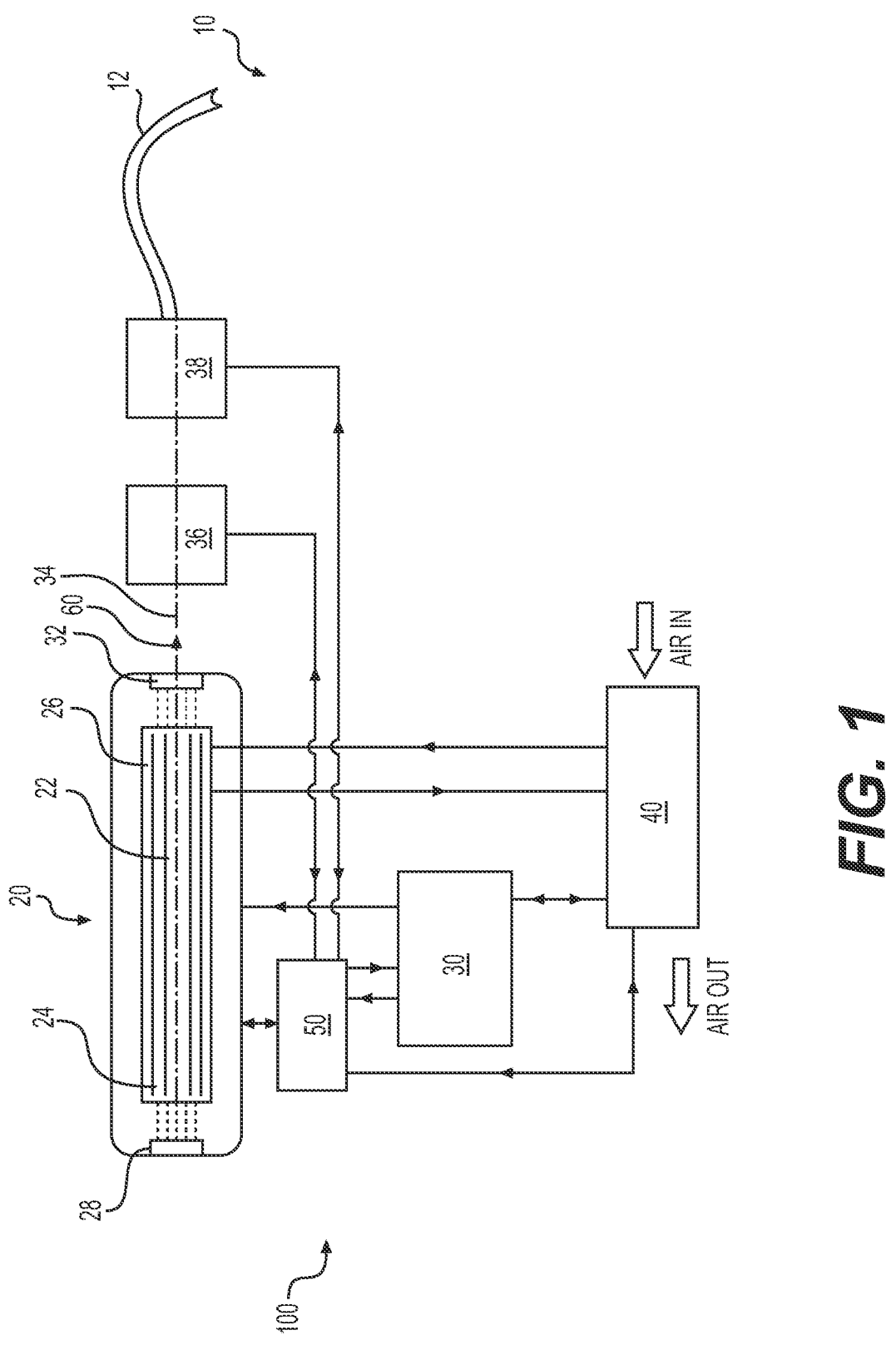
FIG. 1 is a schematic illustration of an exemplary laser system.

FIG. 1 is a schematic illustration of an exemplary laser system 100 of the present disclosure. Laser system 100 is suitable for generating and delivering pulses of laser radiation directly, or through a conventional laser delivery system (e.g., flexible optical fiber 12) to a target site 10 within a subject's body (e.g., a stone within the subject's urinary tract). Laser system 100 includes an oscillator 20 configured to generate and deliver a laser beam in the form of laser pulses 60 to the target site 10 through the optical fiber 12. The oscillator 20 includes a solid-state lasing medium 22 that includes one or more lasing ions (e.g., Ho, Cr, Th, Er, etc.) doped in various concentrations within a host material (e.g., YAG, etc.). In some embodiments, the lasing medium 22 may have a relatively long emission and fluorescence lifetime. As is known to a person of skilled in the art, fluorescence lifetime is a measure of time the electrons of the lasing medium 22 spends in an excited state before returning to its ground state by emitting a photon.

The oscillator 20 may include an optical pump 24 for optically exciting the lasing medium 22 to produce a laser beam. The optical pump 24 may include any known type of device (e.g., flashlamp, arclamp, electrically pumped LED, laser diode, diode-pumped laser, solid state crystal or fiber laser, etc.) used to optically excite the lasing medium 22. The optical pump 24 may be powered by a power supply 30 that includes components to operate the optical pump 24. These components may include, among others, a capacitor for energy storage and discharge, an inductor for pulse shaping, and a trigger circuit for ionizing the optical pump 24.

The power supply 30 may be configured to deliver electrical pulses from the capacitor to operate the optical pump 24. A pump chamber 26 may house both the lasing medium 22 and the optical pump 24, and allow optical radiation to transfer from the optical pump 24 to the lasing medium 22. The pump chamber 26 may also allow for the efficient cooling of both the lasing medium 22 and the optical pump 24. The laser oscillator 20 may include a housing, upon which is mounted the pump chamber 26, a fully reflective optic 28 and a partially reflective optic 32. Both the fully reflective optic 28 and the partially reflective optic 32 may include one or more optical components (lens, mirrors, etc.) of various physical shapes, and may be coated for reflection and/or transmittance of various wavelength(s) of radiation. In some embodiments, these optics 28, 32 may be positioned in adjustable mounts that allow these components to be centered on the path of a laser beam traversing the solid-state lasing medium 22.

A cooling system 40 may supply a coolant to cool heat-producing components of the laser system 100. The liquid or gaseous coolant may be recirculated through the pump chamber 26 in a closed loop to cool the heat-producing components of the oscillator 20. In some embodiments, the cooling system 40 may be cooled by air. In some embodiments, other components of the laser system 100 (e.g., power supply 30) may also be cooled by the coolant of the cooling system 40. It is also contemplated that, in some embodiments, the cooling system 40 may be used to heat the components of the oscillator 20.

The operation of the laser system 100 may be controlled by a controller 50. As known in the art, the controller 50 may include a central processing unit (CPU) and other components that facilitate control of the laser system 100 (e.g., power supply 30, cooling system 40, oscillator 20, etc.) based on user input and/or feedback from sensors/detectors that monitor the performance of the laser system 100. For example, based on user input, the controller 50 may control the power supply 30 to generate electrical pulses of desired characteristics (amplitude, frequency, pulse duration, etc.) to operate the optical pump 24. And, based on the measured temperature of the oscillator 20, the controller 50 may control the operation of the cooling system 40. Since the functions of a controller 50 of a laser system are well known in the art, they are not discussed extensively herein.

During operation of the laser system 100, the controller 50 controls the power supply 30 to direct a current/voltage waveform, or an electrical pulse, having desired characteristics (amplitude, duration, magnitude, etc.) to the optical pump 24. The optical energy generated by the optical pump 24 as a result is coupled to the lasing medium 22. For optimal coupling, the optical pump 24 may be arranged around, and positioned in close contact with, the lasing medium 22. In some embodiments, coupling of optical energy into the lasing medium 22 may be improved through reflections off of the interior surfaces of pump chamber 26. The optical energy from the optical pump 24 raises the energy level of the electrons in the lasing medium 22 to achieve population inversion. Population inversion occurs when more of the electrons of the lasing medium 22 exist in their excited state (i.e., higher energy state) than their ground state (i.e., normal or low energy state). As population inversion is achieved, one or more wavelengths of optical radiation pass multiple times through the lasing medium 22 and are reflected off both the fully reflective optic 28 and the partially reflective optic 32. When the excitation level of the electrons reach a threshold value (referred to in laser physics as the lasing threshold or laser threshold), laser pulses 60 are generated and emitted along the axis 34 of the oscillator 20.

A portion of the emitted laser pulses 60 may be sampled by an optical detector 36 to facilitate monitoring and control of the laser system 100. For example, the controller 50 may use signals from the optical detector 36 (that are indicative of the emitted laser beam) to monitor and control the operation of the oscillator 20, the power supply 30, the cooling system 40 and other components of the laser system 100. The emitted laser pulses 60 may then be directed through one or more optical coupling elements 38 to condition the subsequent outgoing pulses for entrance into the proximal end of the optical fiber 12. The laser pulses 60 are then transmitted through the optical fiber 12 to its distal end that may be placed in contact with (or in close proximity to) a stone (not shown) at the target site 10. At the target site 10, the impinging laser pulses 60 may fragment the stone.

The laser system 100 of FIG. 1 may also include additional components (such as, for example, controllers, mirrors, focusing elements, beam blocking devices, Q-switching or mode-locking elements, etc.) that are well known to people of ordinary skill in the art, and therefore, not illustrated in FIG. 1 and not discussed herein. For example, in some embodiments, the laser system 100 may be further controlled using reflected radiation (or radiation that is rescattered, reemitted, changed in wavelength by the stone material, etc.) from the stone, transmitted back to the proximal end through the fiber 12. Further, in some embodiments, a visible aiming beam (e.g., low power semiconductor diode laser, helium-neon (HeNe) laser, etc.) may be provided to assist in focusing the emitted laser pulses 60 at the target site 10.

Figure 2A:
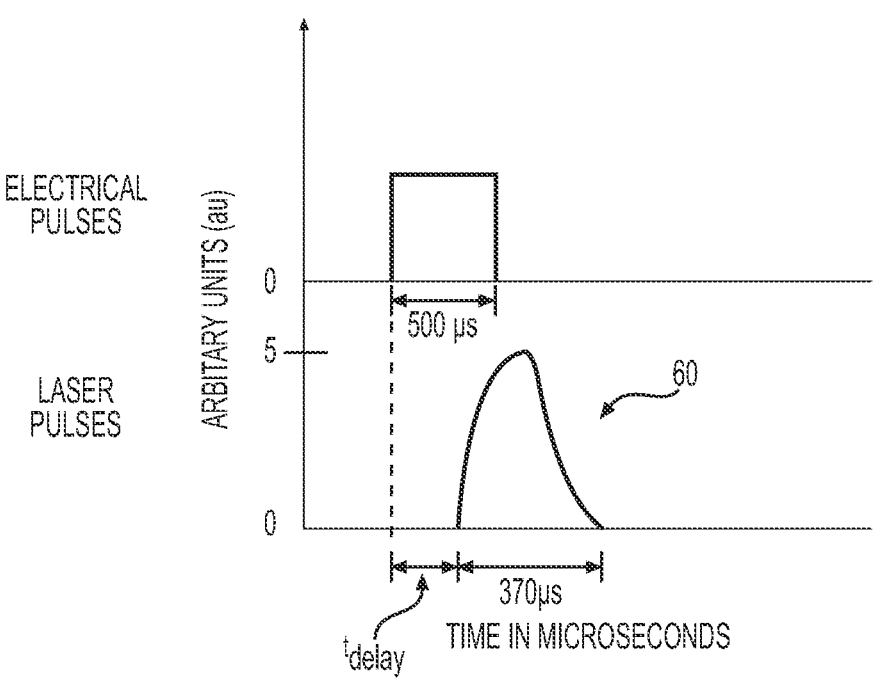
FIGS. 2A and 2B illustrate exemplary discrete laser pulses produced by the laser system of FIG. 1.
Figure 2B:
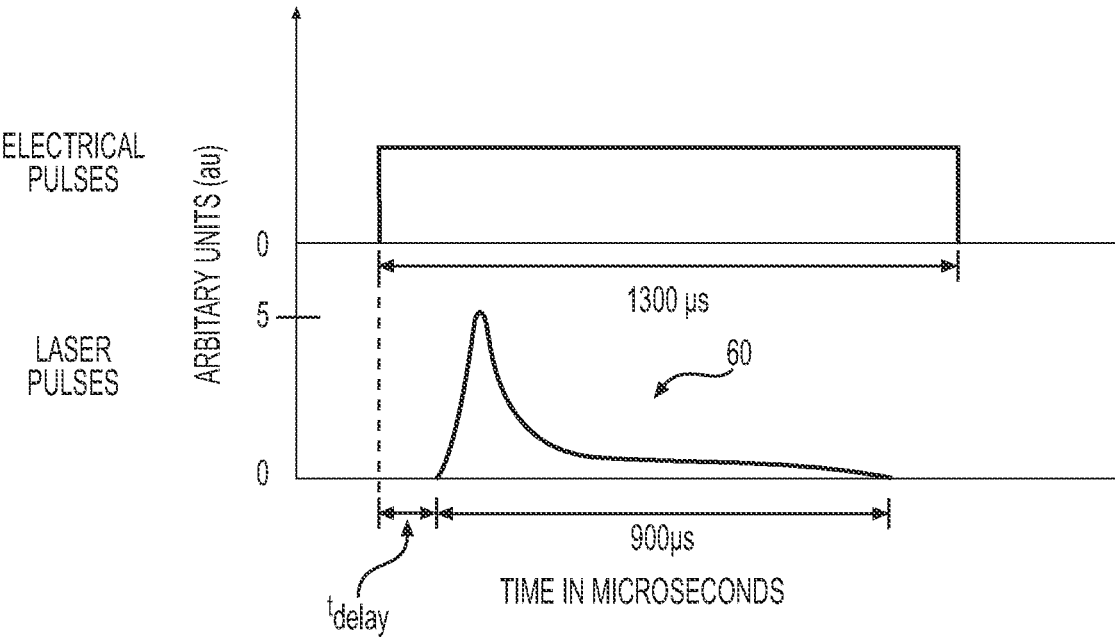

The characteristics (energy, pulse width, power, frequency, etc.) of the emitted laser pulses 60 may depend on the characteristics of the optical pulses generated by the optical pump 24. The characteristics of these optical pulses may depend on the electrical pulses directed to the optical pump 24 from the power supply 30. FIGS. 2A and 2B are simplified charts that illustrate exemplary relationships between an electrical pulse to the optical pump 24 and the resulting laser pulse 60 from the oscillator 20 in a standard operating mode. In these figures, the upper portion illustrates the electrical pulse directed to the optical pump 24, and the lower portion illustrates the resulting laser pulse 60. FIG. 2A illustrates the case when a relatively short electrical pulse is directed to the optical pump 24, and FIG. 2B illustrates the case when a relatively longer electrical pulse is directed to the optical pump 24.

Although the electrical pulses in FIGS. 2A and 2B are illustrated as rectangular pulses, this is merely a simplification. In reality, these pulses may be more rounded because of losses in the components. In contrast with such typical electrical pulses, the corresponding laser pulses 60 (in FIGS. 2A and 2B) have a characteristic shark-fin shape. That is, these laser pulses 60 have a high initial peak followed by a steep decline. The area of the curve in FIGS. 2A and 2B is indicative of the energy of the corresponding laser pulse 60. As can be seen from both FIGS. 2A and 2B, there is a finite time delay ($t_{delay}$) between the start of an electrical pulse and its resulting laser pulse 60. This time delay is related to the time it takes for the lasing medium 22 to reach the lasing threshold. Simplistically, the energy of the electrical pulse in the time period $t_{delay}$ is used to raise the excitation level of the electrons in the lasing medium 22 to the lasing threshold. When this threshold is reached or exceeded, a laser pulse 60 emanates. The time delay may be a function of the energy of the electrical pulse and the laser pulse 60.

Further, as can be seen in both FIGS. 2A and 2B, the emitted laser pulse 60 is shorter (in time scale) than the electrical pulse that generates it. For example, in FIG. 2A, the electrical pulse has a duration of about 500 µs and the laser pulse 60 that results from this electrical pulse is only about 370 μs, and in FIG. 2B, while the electrical pulse has a duration of about 1300 μs the resulting laser pulse 60 only has a duration of about 900 μs. This difference in duration is a result of the energy losses that occur in the oscillator 20 as well as due to reduction in fluorescence lifetime due to stronger pumping and thermal effects. Additionally, as can be seen by comparing FIGS. 2A and 2B, because of the rapidly decaying shape of the laser pulse curve, the increase in energy (area under the laser pulse curve) resulting from a longer electrical pulse is not significant.

Figure 3:
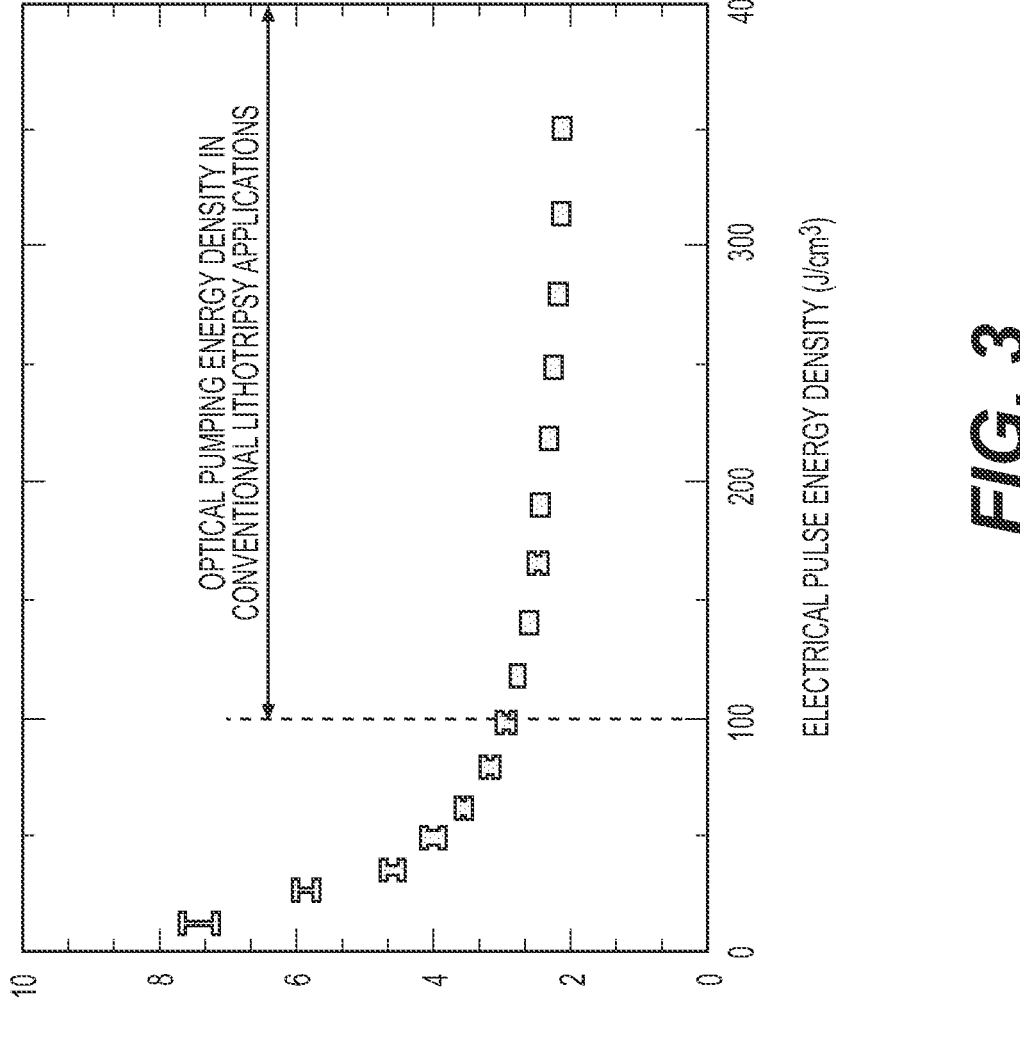
FIG. 3 illustrates the relationship between the fluorescence lifetime and the optical pumping energy in an exemplary laser system.

Conventionally, to increase the energy of the laser pulse, the power (or magnitude) of the electrical pulse (or pumping energy) is increased. Increasing the power of the electrical pulse (and thereby the optical pumping energy) increases the magnitude of the initial peak of the corresponding laser pulse. Further, it is well known that the fluorescence lifetime of a lasing medium may strongly depend on the optical pumping energy. FIG. 3 illustrates the fluorescence lifetime of a CTH:YAG lasing medium as a function of optical pumping energy density. As can be seen from FIG. 3, when a lasing medium 22 is pumped at low energy levels, the fluorescence lifetime of the lasing medium 22 is substantially greater than when it is pumped at high energy levels. For example, when the optical pumping energy density is increased from about 30 J/cm$^3$ to about 300 J/cm$^3$, the fluorescence lifetime of the lasing medium decreased from about 6 millisecond (ms) to about 2 ms. Conventional laser systems use an optical pumping energy between about 100-300 J/cm$^3$ for lithotripsy applications. Thus the efficiency of the laser is reduced due to shorter fluorescence lifetime, especially for long laser pulses with a pulse duration in the range of the fluorescence lifetime.

Additionally, the higher magnitude initial peak resulting from a high power electrical pulse may cause the energy of the laser pulse 60 to, at least momentarily, exceed a desired value. This momentary increase in laser energy may damage optical components of laser system 100 and cause undesirable effects such as retropulsion and large stone fragments (which may have to be removed using additional medical devices such as, for e.g., retrieval baskets).

For some stone fragmentation applications (e.g., "stone dusting" where small fragments of the stone are chipped away and removed by suction), it may be desirable to increase the energy of a laser pulse 60 without causing a sharp energy spike in the initial peak region of the pulse. Contrary to conventional wisdom, in some embodiments of the current disclosure, the energy of the laser pulse is increased by increasing the duration of the laser pulse and decreasing the pumping energy (i.e., power of the electrical pulse) that produces the laser pulse. For example, in some embodiments, the controller 50 may control the energy of the electrical pulse to be below about 50 J/cm$^3$ (to reduce the power of the emitted laser pulse 60) and increase the duration (and therefore, the energy content) of the emitted laser pulse 60 without causing a concomitant increase in the magnitude of the initial peak with high efficiency as the long fluorescence lifetime will not be substantially reduced.

Figure 4A:
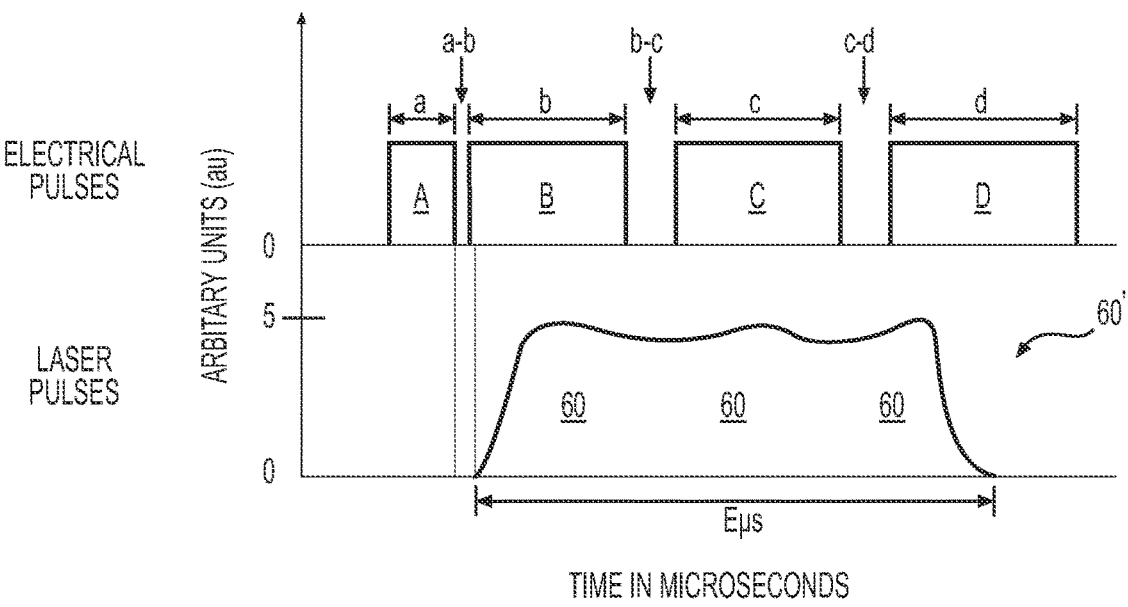
FIG. 4A illustrates an exemplary quasi-continuous laser pulse produced by the laser system of FIG. 1.

FIG. 4A is a simplified chart that illustrates the relationship between electrical pulses and the resulting laser pulse in one embodiment of the present disclosure. In this embodiment, multiple temporally spaced-apart electrical pulses (marked A, B, C, D) are directed from the power supply 30 to the optical pump 24 such that the laser pulse resulting from these temporally spaced-apart electrical pulses have a quasi-continuous waveform (quasi-continuous laser pulse 60'). With reference to FIG. 4A, in some embodiments, the initial electrical pulse to the optical pump 24 may be a pre-pulse (marked A) that is configured to raise the energy level of the lasing medium 22 to a value that is close to, but just below, the lasing threshold (e.g., to about 80-99% of the lasing threshold). Pre-pulse A does not result in an emitted laser pulse 60 since the excitation caused by the pre-pulse does not reach the lasing threshold. However, at the end of the pre-pulse A at time $t_1$, the electrons of the lasing medium 22 may be primed to emit radiation in the form of a laser pulse 60 upon further addition of a small amount of energy. A sequence of three electrical pulses (B, C, D) is then provided to the optical pump 24 in a short interval to initiate the quasi-continuous laser pulse 60' from the oscillator 20. In general, the plurality of pulses A, B, C, D may be spaced apart such that a subsequent electrical pulse is within the fluorescence lifetime of its immediately preceding pulse (i.e., pulse B is within the fluorescence lifetime of pulse A, pulse C is within the fluorescence lifetime of pulse B, etc.).

In general, the shape of the quasi-continuous laser pulse 60' depends on the characteristics of laser system 100 (e.g., power, spacing, duration, etc. of the electrical pulses, material of the lasing medium, etc.). In some embodiments, as illustrated in FIG. 4A, the quasi-continuous laser pulse 60' that results from the spaced-apart electrical pulses A, B, C, D may be a continuous waveform having an extended duration of E μs. As used herein, a laser pulse having a continuous waveform is a laser pulse that may vary in magnitude from any maximum value to any non-zero minimum value during the duration of the pulse. That is, a continuous waveform has a magnitude of zero only at its terminal ends. In the embodiment of FIG. 4A, the quasi-continuous laser pulse 60' is produced by merging (or combining) together individual laser pulses 60 produced by the individual electrical pulses B, C, and D. In some embodiments, the laser pulses 60 produced by each electrical pulse of a set of spaced-apart electrical pulses may not be merged to produce a quasi-continuous laser pulse 60'. For example, in some embodiments, a quasi-continuous laser pulse 60' may be produced by only merging together the laser pulses produced by electrical pulses B and C. If the pulse duration of a laser pulse produced by an individual electrical pulse (e.g., B and C) is 250 μm, the duration of a quasi-continuous laser pulse 60' may be more than 250 μm and less than 500 μm (produced, for example, by combining the laser pulses from the two electrical pulses).

As illustrated in FIG. 4A, after pre-pulse A, the further addition of a small amount of energy to the already primed lasing medium 22 results in the initiation of a quasi-continuous laser pulse 60' at time $t_2$. The duration (a, b, c, d) of the electrical pulses, and the spacing (a-b, b-c, c-d) between them, may depend upon the characteristics of the laser system 100 and the power of the electrical pulses. In general, the duration a of the pre-pulse A may be such that the lasing medium 22 reaches an excitation level between about 80-99% (but below 100%) of the lasing threshold at the end of pre-pulse A. And, the spacing a-b between pulses A and B, and B and C, may be such that energy dissipation from the primed lasing medium 22 is minimized. As is known in the art, a significant amount of energy remains stored in the lasing medium 22 at the end of each laser pulse (e.g., laser pulse 60 resulting from electrical pulse B), when population inversion ceases to exist. If the spacing b-c between electrical pulses B and C is too high (but still within the fluorescence lifetime), this stored energy would be wasted in sub-threshold radiative and non-radiative decay prior to pumping by electrical pulse C. However, if electrical pulse C begins soon after electrical pulse B, much of the stored energy can be utilized in the generation of the next laser pulse 60, thereby decreasing the pump energy needed to achieve population inversion.

In different embodiments of the present disclosure, the duration a, b, c, d and the spacing a-b, b-c, c-d between the electrical pulses A, B, C, B may vary between about 10-1000 μs, and the resulting duration of the quasi-continuous laser pulse 60' may be between about 250 us and 10 millisecond (ms). In some embodiments, one or more of the duration a, b, c, d may be between about 10-200 μs (or 10-300 μs), and one or more of the spacing a-b, b-c, c-d may be between about 10-100 μs (or 10-200 μs). In the embodiment of FIG. 4, the duration a of the pre-pulse A may be between about 30 and 300 μs; the spacing a-b between pulses A and B may be between about 10 and 100 μs; the duration of the pulses B, C, and D may be between about 10 and 500 μs; the spacing b-c and c-d between the electrical pulses B, C, and D may be between about 10 and 100 μs; and the resulting duration E of the resulting quasi-continuous laser pulse 60' may be between about 600 and 1500 μs. In some embodiment, the power of the resulting quasi-continuous laser pulse 60' may be between about 100 and 1 KW.

Figure 4B:
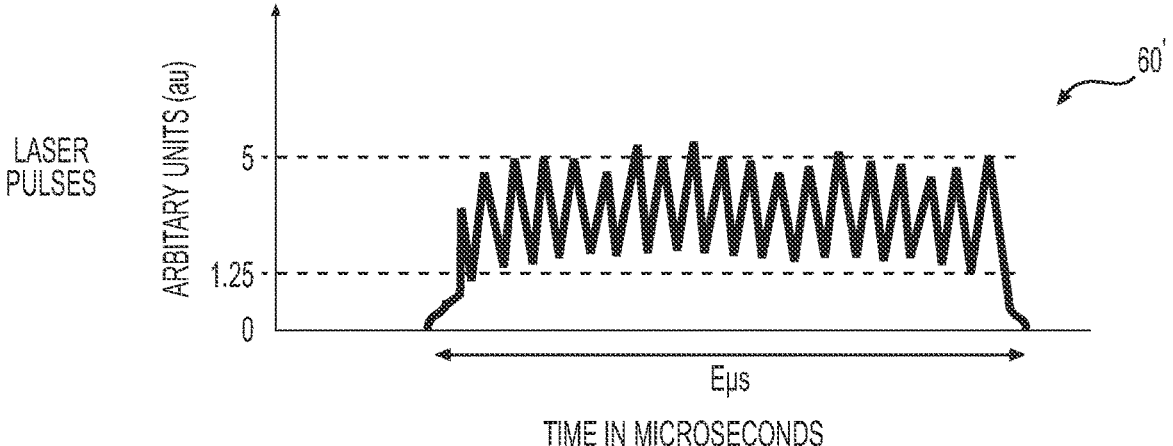
FIG. 4B illustrates another exemplary quasi-continuous laser pulse produced by the laser system of FIG. 1.

It should be noted that the illustrated shape in FIG. 4A, of the quasi-continuous laser pulse 60' having a smooth continuous waveform, is only exemplary. FIG. 4B illustrates another exemplary quasi-continuous laser pulse 60' having a continuous waveform that results from a plurality of temporally spaced-apart electrical pulses. As illustrated in FIG. 4B, the magnitude of the quasi-continuous laser pulse 60' may vary from an average maximum value of about 5 arbitrary units (au) (Joules, etc.) to a minimum average value of about 1.25 au (i.e. 25% of the maximum value) in a duration of E μs. However, the waveform has a zero magnitude only at its terminal ends and has a non-zero magnitude everywhere within its duration. Although the magnitude of a continuous waveform between its terminal ends is always non-zero, it should be noted that the maximum and minimum values illustrated in FIG. 4B are only exemplary. In general, the minimum value may be any percentage (10%, etc.) of the maximum value.

In FIGS. 4A and 4B, the laser pulses 60 resulting from each electrical pulse merge together to produce a quasi-continuous laser pulse 60' in the form of a continuous waveform. However, producing an output laser pulse of a continuous waveform is not a limitation. In some embodiments, for example, where a lasing medium 22 with faster energy transfer processes compared to CTH:YAG is used (e.g. Er:YAG; Nd:YAG; Er:YLF, etc.), the laser pulses 60 that result from the series of input electrical pulses may be temporally spaced apart. For example, with reference to FIG. 4A, if the spacing b-c and c-d between electrical pulses B, C, and D are less than or equal to about 100 μs, the oscillator 20 may output a quasi-continuous laser pulse 60' in the form of a continuous waveform. However, if the electrical pulses B, C, and D are spaced apart greater than 100 μs, the oscillator 20 may output a quasi-continuous laser pulse 60' which comprises distinct temporally spaced-apart laser pulses 60 (i.e., which collectively do not form a continuous waveform). However, since the frequency (and thereby the repetition rate) of these spaced-apart laser pulses 60 is greater than about 1 kHz (at room temperature), the resulting spaced-apart laser pulses 60 may resemble, and effectively be, a substantially continuous laser pulse. Thus, in the current disclosure, the term quasi-continuous laser pulse is used to collectively refer to both (a) multiple laser pulses 60 merged together to form a laser pulse having a continuous waveform (e.g., similar to those illustrated in FIGS. 4A and 4B), and (b) multiple laser pulses 60 temporally spaced apart from each other and having a frequency greater than about 1 kHz.

Figure 5:
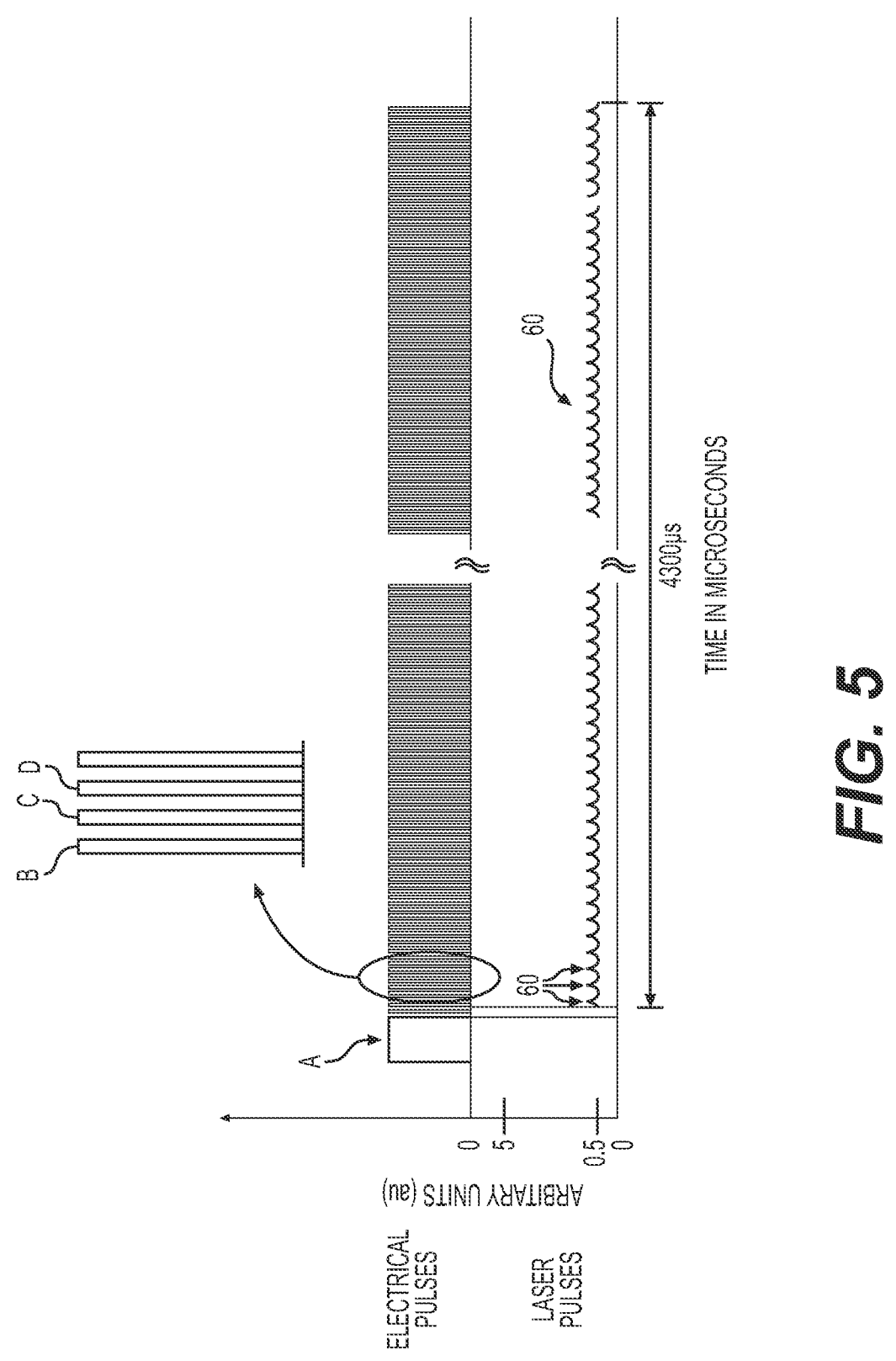
FIG. 5 illustrates another exemplary quasi-continuous laser pulse produced by the laser system of FIG. 1.

FIG. 5 is a simplified chart that illustrates another exemplary quasi-continuous laser pulse 60' in the form of a continuous waveform that results from a plurality of temporally spaced-apart electrical pulses. In the embodiment of FIG. 5 (as in the embodiment of FIGS. 4A and 4B), an initial pre-pulse A excites the lasing medium 22 to just below its lasing threshold. That is, at the end of the pre-pulse A, while a laser pulse 60 does not yet emanate from the oscillator 20, the addition of small amount of added energy will cause a laser pulse to be emitted. Following pre-pulse A, the optical pump 24 is pumped using a relatively longer sequence of temporally spaced-apart electrical pulses B, C, D, etc. (for example, about 50 pulses) that each have an energy density of less than about 50 J/cm$^3$, a duration of about 50 μs, and are spaced-apart from its adjacent pulses by about 50 μs. This sequence of temporally spaced-apart electrical pulses used to drive the optical pump 24 may be referred to herein as digitized electrical pulses or digital pumping. As a result of such optical pumping, a quasi-continuous laser pulse 60' (that comprises a series of laser pulses 60 merged to form of a continuous waveform) having a relatively long duration (e.g., about 4300 μs), emanates from the oscillator 20. It should be noted that this laser pulse duration is only exemplary. It is contemplated that using digitized electrical pulses having different characteristics (number, duration, spacing, etc.), the output laser pulse duration may be varied to any value between about 250 μs to 10 ms.

In general, the magnitude of the electrical pulses may be configured to produce laser pulses 60 having any magnitude. However, as explained previously, there are several advantages (increased fluorescence lifetime, reduced retropulsion, etc.) to reducing the pumping energy and the resulting laser power. Therefore, as illustrated in FIG. 5, in some embodiments, the energy density of the electrical pulses may be kept below 50 J/cm$^3$ to produce a quasi-continuous laser pulse 60' having a smaller magnitude (e.g., that varies from about 0.5-0.25 au) and a longer duration (e.g., about 4.3 milliseconds (ms)) as compared to the laser pulse 60 of, for example, FIG. 2A. Although the magnitude of the quasi-continuous laser pulse 60' (of FIG. 5) is smaller than laser pulse 60 (of FIG. 2A), it's substantially longer duration makes the total energy content of the quasi-continuous laser pulse 60' more than, or equal to, that of laser pulse 60.

For example, to produce a laser beam having energy of 500 mJ, in a conventional CTH:YAG laser the lasing medium is optically pumped with an energy of between about 100-500 J/cm$^3$ per pulse to yield a laser pulse having about 2.5-1.0 KW peak power and a duration of about 200-500 μs. In contrast, to produce a laser beam having the same energy (i.e., 500 mJ), an exemplary laser system of the current disclosure may pump the lasing medium multiple times as described above (e.g., 30-100 times) with an energy of between about 2-50 J/cm$^3$ to create a laser pulse having between about 70-150 W peak power (e.g., 100-130 W) to produce a quasi-continuous laser pulse 60' having a duration of about 4.5 ms. This smaller magnitude and longer duration laser pulse 60' may increase the efficiency of the laser system 100 by minimizing undesirable effects such a retropulsion. The lower magnitude and longer duration quasi-continuous laser pulse 60' may be used for medical applications, such as stone dusting, where dust-sized particles of the stone are desired to be removed without blasting the stone into multiple large sized pieces.

To compare the performance of a quasi-continuous laser pulse 60' (produced by an exemplary laser system 100 of the current disclosure) with a conventional laser pulse 60 (produced by a conventional laser system) for stone ablation applications, cavitation dynamics of the two pulses in water were studied with a high-speed camera. Both the laser systems were setup such that the energy of the laser pulse produced by the respective laser system was substantially the same (about 1000-1300 mJ). While both the laser pulses had the same energy, the quasi-continuous laser pulse 60' had a duration of about 4100 µs (resulting from a series of spaced-apart electrical pulses) and the conventional laser pulse 60 had a duration of about 310 µs. Significant differences were observed in these studies. While the cavitation bubble produced by the conventional laser pulse 60 rapidly grew in size achieving its maximum size approximately at the end of the pulse, the bubble of the quasi-continuous laser pulse 60' grew more slowly reaching only approximately 40% of the size of the conventional pulse bubble. As a consequence, the collapse of the quasi-continuous laser pulse bubble did not emit as strong an acoustic shock wave as with the case of the conventional pulse bubble collapse. Correspondingly it could be proven that the retropulsion effect on a stone (that each laser pulse is applied to) can be greatly reduced in the case of the quasi-continuous laser pulse 60' compared with the conventional laser pulse 60.

Furthermore, an observed unique feature of the cavitation dynamics of the quasi-continuous laser pulse 60' was a long-lived (approximately 2.6 ms) permanent cavitation channel that formed after the initial turbulences associated with the bubble formation, collapse and rebound settled down. In this channel the density of water (water vapor) and the corresponding absorption of the laser pulse energy is greatly reduced. As a result, it could be shown that the controlled ablation of stone material layer-by-layer (or the "stone dusting" effect) will be significantly enhanced.

Although FIGS. 4A and 5 illustrate a pre-pulse A comprising of a single electrical pulse, this is not a limitation. In some embodiments, the pre-pulse A may also comprise multiple smaller duration pre-pulses (e.g., similar to electrical pulses B, C, etc.) that each incrementally increases the excitation level of the lasing medium 22 to a value just below the lasing threshold. Further, although the magnitude of the electrical pulses A, B, C, D are illustrated as being the same in FIGS. 4A and 5, this also is only exemplary. In general, these input electrical pulses may have the same or different magnitudes. As described previously, the power of the pre-pulse A may be adapted to increase the energy of the lasing medium 22 to a value just below its lasing threshold. In some embodiments, the magnitude of the immediately following electrical pulse (i.e., B) may be smaller than pre-pulse A (for e.g., adapted to increase the energy of the lasing medium 22 to just above the lasing threshold to initiate laser emission).

In the embodiment of FIG. 5, both the duration of the electrical pulses (B, C, D, etc.), and the spacing between them, are a constant. Such an electrical pulse profile may produce a quasi-continuous laser pulse 60' having a profile comprising a uniform repeated pattern as illustrated in FIG. 5. However, a constant duration and spacing of electrical pulses is not a requirement. In some embodiments, one or all of the duration of the electrical pulses, the spacing between the electrical pulses, and the magnitude of the electrical pulses may be varied to tailor the resulting laser pulse 60' profile as desired. That is, the pattern of optical pumping of the lasing medium 22 may be configured to modulate (increase, decrease, etc.) the pulse width and shape of the resulting laser beam.

Figure 6:
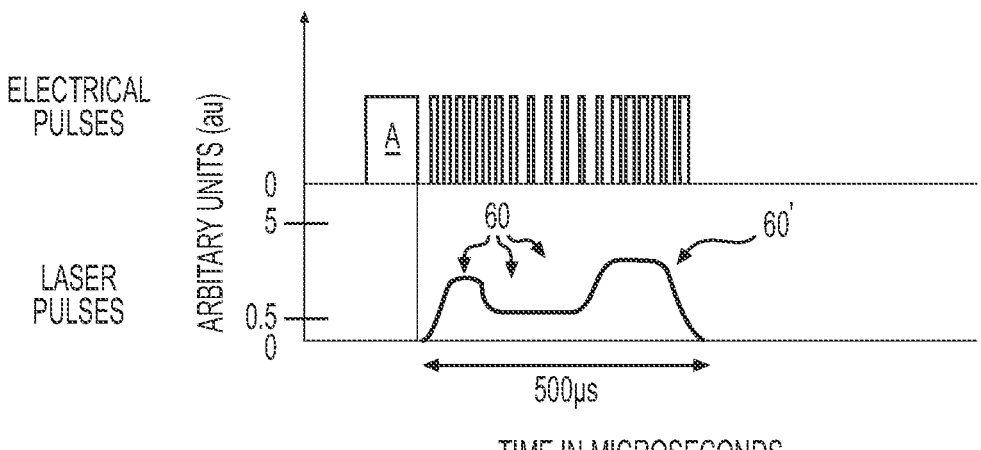
FIG. 6 illustrates an exemplary tailored laser pulse produced by the laser system of FIG. 1.

FIG. 6 is a simplified chart that illustrates an exemplary tailored laser pulse 60' profile resulting from a preselected pattern of electrical pulses. Similar to the previous embodiments, the pre-pulse A may raise the excitation level of the lasing medium 22 to a value just below the lasing threshold (i.e., to about 80-99% of the lasing threshold). Pre-pulse A may be followed with a plurality of temporally spaced-apart electrical pulses to nudge the excitation level of the lasing medium 22 over the lasing threshold, and start emission of the laser pulses 60. The spacing between the electrical pulses, and the duration of the electrical pulses, in different regions may be selected to produce a laser pulse 60' profile having any desired shape. For example, the series of seemingly digital electrical pulses directed to the optical pump 24 may be such that, the spacing between the pulses (and/or the duration of the pulses) in one region of the series may be different from that in another region to create a difference in the shape of the resulting waveform corresponding to the two regions. Thus, by modulating the pattern of electrical pulses used to pump the lasing medium 22, the output laser pulse can be controlled to have any desired shape and profile.

In some embodiments, a control system (e.g., controller 50) of the laser system 100 may determine a suitable of pattern of electrical pulses based on a user desired laser pulse profile, and direct these electrical pulses to the optical pump 24. The oscillator 20 of the laser system 100 may then output a quasi-continuous laser pulse 60' having a profile similar to the user desired pulse profile. For example, the user may input (using a keypad, screen, or other input device) a desired laser pulse profile (that the user knows, based on prior knowledge, experience, etc., to be particularly suitable for a medical procedure) to the control system. And, based on known characteristics of the laser system 100, the control system may determine the pattern of electrical pulses that will produce the user desired output. Alternatively or additionally, in some embodiments, a user may determine the pattern of electrical pulses to produce a desired laser pulse profile. In general, any characteristic (duty cycle, frequency, pulse duration, power, etc.) of the electrical pulses may be varied in different regions to produce any tailored laser pulse profile.

Figure 7:
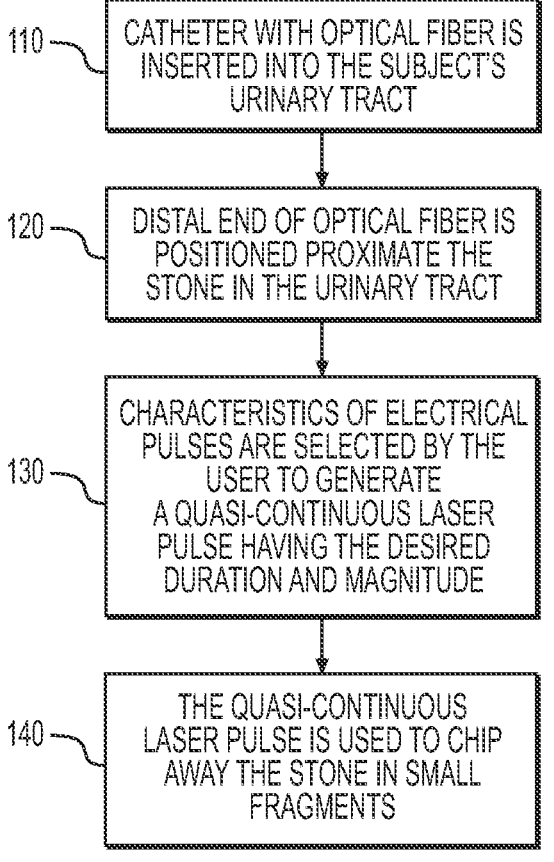
FIG. 7 illustrates an exemplary method of using the laser system of FIG. 1 in an exemplary medical procedure.

FIG. 7 is a flow chart that illustrates an exemplary method of using the laser system 100 of FIG. 1 in laser lithotripsy procedure. The subject is prepared for the medical procedure, and suitable catheter (endoscope, ureteroscope, etc.), with the optical fiber 12 extending therethrough, is inserted into the subject's body through an orifice (step 110). The catheter may then then maneuvered within the body such that the distal end of the optical fiber 12 is positioned proximate the stone (step 120). The user may then input the characteristics (duration, magnitude, spacing, pattern, etc.) of the electrical pulses in controller 50 to generate a quasi-continuous laser pulse 60' having the desired profile, duration, and magnitude (step 130). These characteristics may be selected by the user based on prior experience and knowledge of the laser system 100. The generated quasi-continuous laser pulse 60' may then be used to separate small pieces from the stone (step 140).

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A laser system, comprising:
a power supply configured to generate a plurality of electrical pulses;
an optical pump configured to generate optical energy in response to the plurality of electrical pulses;
a lasing medium optically coupled to the optical pump, the lasing medium configured to output laser pulses in response to the optical energy; and
a controller coupled to the power supply, the controller configured to cause the power supply to generate the plurality of electrical pulses,
wherein the plurality of electrical pulses comprises:
one or more electrical pre-pulses configured to cause the optical pump to generate a first portion of the optical energy, the first portion of the optical energy configured to excite the lasing medium to an energy level below a lasing threshold of the lasing medium, and
a plurality of electrical excitation-pulses configured to cause the optical pump to generate a second portion of the optical energy, the second portion of the optical energy to excite the lasing medium above the lasing threshold of the lasing medium and output a plurality of laser pulses.

2. The laser system of claim 1, wherein the plurality of laser pulses overlaps to form a quasi-continuous laser pulse.

3. The laser system of claim 2, wherein a pulse width of the quasi-continuous laser pulse is between 250 microseconds (μs) to 10 milliseconds (ms).

4. The laser system of claim 2, wherein a power of the quasi-continuous laser pulse is between 100 watts (W) and 1 kilowatt (kW).

5. The laser system of claim 1, wherein each electrical pulse of the plurality of electrical pulses has a pulse width between 10 microseconds (μs) and 1000 μs.

6. The laser system of claim 5, wherein the pulse width of each electrical pulse of the plurality of electrical pulses is the same.

7. The laser system of claim 1, wherein a pulse delay between adjacent electrical pulses of the plurality of electrical pulses is between 10 microseconds (μs) and 1000 μs.

8. The laser system of claim 7, wherein the pulse delay between each of the adjacent electrical pulses is the same.

9. The laser system of claim 1, wherein the plurality of laser pulses has a frequency greater than or equal to 1 kilohertz (kHz).

10. The laser system of claim 1, wherein the lasing medium includes Ho:YAG, Tm:YAG, Tm:Ho:YAG, Er:YAG, Er:YLF, Nd:YAG, Tm-fiber, and/or CTH:YAG.

11. A laser system
a power supply configured to generate a plurality of electrical pulses;
an oscillator comprising:
an optical pump configured to generate optical energy in response to the plurality of electrical pulses, and
a lasing medium configured to receive the optical energy;
a cooling sub-system configured to cool the oscillator; and
a controller coupled to the power supply, the controller configured to cause the power supply to generate the plurality of electrical pulses, wherein the plurality of electrical pulses comprises:
one or more electrical pre-pulses configured to cause the optical pump to generate a first portion of optical energy, the first portion of the optical energy configured to excite the lasing medium to an energy level below a lasing threshold of the lasing medium, and
a plurality of electrical excitation-pulses configured to cause the optical pump to generate a second portion of the optical energy, the second portion of the optical energy to excite the lasing medium above the lasing threshold of the lasing medium and output a plurality of laser pulses.

12. The laser system of claim 11, wherein the plurality of laser pulses overlaps to form a quasi-continuous laser pulse and wherein a pulse width of the quasi-continuous laser pulse is between 250 microseconds (μs) to 10 milliseconds (ms).

13. The laser system of claim 11, wherein the plurality of laser pulses overlaps to form a quasi-continuous laser pulse and wherein a power of the quasi-continuous laser pulse is between 100 watts (W) and 1 kilowatt (kW).

14. The laser system of claim 11, wherein each electrical pulse of the plurality of electrical pulses has a pulse width between 10 microseconds (μs) and 1000 μs, wherein a pulse delay between adjacent electrical pulses of the plurality of electrical pulses is between 10 microseconds (μs) and 1000 μs, or wherein each electrical pulse of the plurality of electrical pulses has a pulse width between 10 microseconds (μs) and 1000 μs and a pulse delay between adjacent electrical pulses of the plurality of electrical pulses is between 10 microseconds (μs) and 1000 μs.

15. The laser system of claim 11, wherein a pulse width of each electrical pulse of the plurality of electrical pulses is the same, wherein a pulse delay between adjacent electrical pulses of the plurality of electrical pulses is the same, or wherein the pulse width of each electrical pulse of the plurality of electrical pulses is the same and the pulse delay between adjacent electrical pulses of the plurality of electrical pulses is the same.

16. The laser system of claim 11, wherein the lasing medium includes Ho:YAG, Tm:YAG, Tm:Ho:YAG, Er:YAG, Er:YLF, Nd:YAG, Tm-fiber, and/or CTH:YAG.

17. The laser system of claim 11, wherein the plurality of electrical pulses comprises a first set of electrical pulses and a second set of electrical pulses and wherein at least one of (i) a pulse width, (ii) a pulse delay, or (iii) a pulse magnitude of the first set of pulses is different from the second set of pulses.

18. A method for a controller of a laser system comprising a power supply configured to generate a plurality of electrical pulses, an optical pump configured to generate optical energy in response to the plurality of electrical pulses, and a lasing medium configured to receive the optical energy, the method comprising:
sending control signals to the power supply, the control signals configured to cause the power supply to generate a plurality of electrical pulses,
wherein the plurality of electrical pulses comprises:
one or more electrical pre-pulses configured to cause the optical pump to generate a first portion of optical energy, the first portion of the optical energy configured to excite the lasing medium to an energy level below a lasing threshold of the lasing medium, and
a plurality of electrical excitation-pulses configured to cause the optical pump to generate a second portion of the optical energy, the second portion of the optical energy to excite the lasing medium above the lasing threshold of the lasing medium and output a plurality of laser pulses.

19. The method of claim 18, wherein each electrical pulse of the plurality of electrical pulses has a pulse width between 10 microseconds (μs) and 1000 μs, wherein a pulse delay between adjacent electrical pulses of the plurality of electrical pulses is between 10 microseconds (μs) and 1000 μs, or wherein each electrical pulse of the plurality of electrical pulses has a pulse width between 10 microseconds (μs) and 1000 μs and a pulse delay between adjacent electrical pulses of the plurality of electrical pulses is between 10 microseconds (μs) and 1000 μs.

20. The method of claim 18, wherein a pulse width of each electrical pulse of the plurality of electrical pulses is the same, wherein a pulse delay between adjacent electrical pulses of the plurality of electrical pulses is the same, or wherein the pulse width of each electrical pulse of the plurality of electrical pulses is the same and the pulse delay between adjacent electrical pulses of the plurality of electrical pulses is the same.

* * * * *